(12) United States Patent
Pe'ery et al.

(10) Patent No.: US 9,271,998 B2
(45) Date of Patent: Mar. 1, 2016

(54) METHOD OF INHIBITING NONSENSE-MEDIATED MRNA DECAY

(71) Applicant: Rutgers, The State University of New Jersey, New Brunswick, NJ (US)

(72) Inventors: Tsafi Pe'ery, Montclair, NJ (US); Michael B. Mathews, Montclair, NJ (US); Mainul Hoque, North Arlington, NJ (US); Hartmut M. Hanauske-Abel, Edgewater, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/082,346

(22) Filed: Nov. 18, 2013

(65) Prior Publication Data

US 2014/0073685 A1 Mar. 13, 2014

Related U.S. Application Data

(63) Continuation of application No. 12/840,270, filed on Jul. 20, 2010, now Pat. No. 8,603,814.

(60) Provisional application No. 61/271,409, filed on Jul. 20, 2009.

(51) Int. Cl.
| | | |
|---|---|---|
| *A61K 31/713* | (2006.01) | |
| *A61K 31/426* | (2006.01) | |
| *A61K 31/44* | (2006.01) | |
| *A61K 31/4412* | (2006.01) | |
| *A61K 31/4418* | (2006.01) | |

(52) U.S. Cl.
CPC ............ *A61K 31/713* (2013.01); *A61K 31/426* (2013.01); *A61K 31/44* (2013.01); *A61K 31/4412* (2013.01); *A61K 31/4418* (2013.01)

(58) Field of Classification Search
CPC ... A61K 31/713; A61K 31/426; A61K 31/44; A61K 31/4412; A61K 31/4418
See application file for complete search history.

(56) References Cited

U.S. PATENT DOCUMENTS

| | | |
|---|---|---|
| 2,540,218 A | 2/1951 | Shaw |
| 4,797,409 A | 1/1989 | Lohaus et al. |
| 5,087,616 A | 2/1992 | Myers et al. |
| 5,849,587 A | 12/1998 | Hanauske-Abel et al. |
| 7,049,328 B2 | 5/2006 | Spino et al. |
| 2006/0275762 A1 | 12/2006 | Saigo et al. |
| 2007/0031844 A1 | 2/2007 | Khvorova et al. |

FOREIGN PATENT DOCUMENTS

| | | |
|---|---|---|
| WO | 2011/005566 A2 | 1/2011 |

OTHER PUBLICATIONS

Woeller, et al. "NMD resulting from encephalomyocarditis virus IRES-directed translation initiation seems to be restricted to CBP80/20-bound mRNA." EMBO Rep. 9(5): 446-51. (2008).
Hogue, et al. "Inhibition of HIV-1 gene expression by Ciclopirox and Deferiprone, drugs that prevent hypusination of eukaryotic initiation factor 5A." Retrovirology 6:90. (2009).
Wadhwa, et al. "Receptor Mediated Glycotargeting". Journal of Drug Targeting 3: 111-127. (1995).
Olivieri, et al., Long-term Safety and Effectiveness of Iron-Chelation Therapy with Deferiprone for Thalassemia Major, The New England Journal of Medicine 339(7): 417-423. (1998).
Brunskill, et al., Oral deferiprone for iron chelation in people with thalassaemia (Review), The Cochrane Library, Issue 1, pp. 1-53. (2009).

*Primary Examiner* — Samantha Shterengarts
(74) *Attorney, Agent, or Firm* — Fox Rothschild LLP

(57) ABSTRACT

Provided are methods for treating a NAD comprising administering to a patient suffering from a NAD a composition comprising an eIF5A inhibitor compound in an amount effective to prevent intracellular hypusination of eIF5A, whereby gene expression of NMD-susceptible mRNA is increased.

17 Claims, 6 Drawing Sheets

METHOD OF INHIBITING NONSENSE-MEDIATED MRNA DECAY

CROSS REFERENCE TO RELATED APPLICATIONS

The instant application is a continuation of U.S. patent application Ser. No. 12/840,270, filed Jul. 20, 2010, which claims 35 U.S.C. §119(e) priority to U.S. Provisional Patent Application Ser. No. 61/271,409 filed Jul. 20, 2009. The foregoing disclosures are hereby incorporated by reference in their entireties.

FIELD OF THE INVENTION

The present invention relates to methods of treating nonsense-associated diseases and inhibiting nonsense-mediated mRNA decay by targeting the pathway of activity associated with eukaryotic initiation factor 5A ("eIF5A").

BACKGROUND OF THE INVENTION

Nonsense-mediated decay ("NMD") is a cellular mechanism that selectively degrades faulty messenger RNA ("mRNA") containing an out-of-place stop (nonsense) codon. If translated, such mRNAs would produce a shortened version of the encoded protein. The NMD surveillance mechanism reduces or prevents the formation of these defective proteins and peptides. While NMD helps to protect against occasional mistakes that occur during RNA production, it also contributes to a number of genetic disorders collectively termed nonsense-associated diseases ("NADs"). Examples of NADs are cystic fibrosis and Hurler's syndrome. Depending on the gene affected and the mutation, prematurely terminated proteins may have low biological activity, no biological activity, or may even be harmful to biological functions.

In NADs there is usually an insufficient amount of the full-length protein as a result of two processes: (1) the destruction of the defective mRNA by NMD; and (2) the synthesis of truncated protein from mRNA that escapes the destruction. Currently, there are a number of drugs that are partially effective against NADs and function by suppressing nonsense codon recognition (i.e., inhibition of process (2)). NMD is triggered by a premature stop codon located at least 50-55 nucleotides upstream of a splice junction in a multi-exon mRNA. Several proteins are involved in NMD, such as Upf1, an essential protein that directly controls mRNA decay, and eIF5A, a eukaryotic initiation factor that is tightly associated with actively translated ribosomes and is an RNA-binding protein. eIF5A is the only protein known to contain the amino acid hypusine. The protein usually occurs in two isoforms, of which eIF5A-1 is usually the more abundant.

Currently, there are a number of compounds that are partially effective against NADs and function by suppressing nonsense codon recognition. While recent reports also indicate involvement of NMD in NADs and certain compounds that suppress NMD function, there is a need in the art for the further characterization of the NMD mechanism associated with various NADs, particularly with respect to inhibitors of eIF5A. There also remains a need for compounds and methods that repress NMD and thereby significantly increase the level of NMD-susceptible mRNA, thereby potentially mitigating NAD symptoms. The instant invention addresses these needs.

SUMMARY OF THE INVENTION

The present invention relates to methods for treating a NAD comprising administering to a patient suffering from a NAD a composition comprising an eIF5A inhibitor compound in an amount effective to prevent intracellular hypusination of eIF5A, whereby gene expression of NMD-susceptible mRNA is increased.

In one embodiment, the present inventive method comprises administering a composition comprising a compound of formula (I):

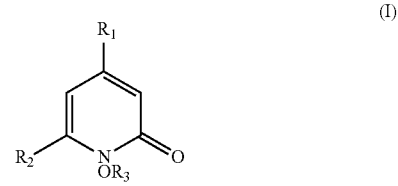

wherein
$R_1$ is $(C_1-C_6)$alkyl;
$R_2$ is $(C_1-C_{10})$ straight or branched alkyl, $(C_3-C_6)$cycloalkyl or phenoxy$(C_1-C_3)$alkyl, where the phenoxy group is substituted by substituted or unsubstituted phenoxy; and
$R_3$ is hydrogen or a pharmacologically acceptable salt.

In another embodiment, the present inventive method comprises administering a composition comprising a compound of formula (II):

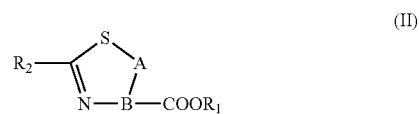

wherein
$R_1$ is hydrogen or a pharmacologically acceptable salt;
$R_2$ is ortho hydroxyl-substituted phenyl or pyridyl, where the phenyl or pyridyl group is otherwise unsubstituted or substituted with 1 to 3 additional substituents selected from the group consisting of $(C_1-C_6)$alkyl, phenyl, $(C_1-C_6)$alkoxy, halogen, or hydroxyl;
A-B is —$CH_2$—$CR_3$— or —CH=CH—; and
$R_3$ is hydrogen or $(C_1-C_6)$alkyl.

In another embodiment, the present inventive method comprises administering a composition comprising a compound of formula (III) or (IV):

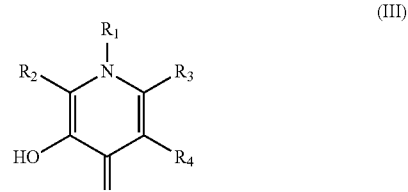

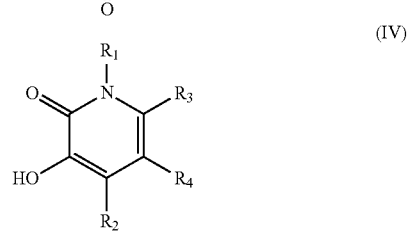

wherein $R_1$, $R_2$, $R_3$, and $R_4$ each individually represent a hydrogen, an alkyl, alkenyl, or alkoxy group containing 1 to about 8 carbon atoms, an aryl, arylaklyl, or cycloalkyl group containing about 5 to 12 carbon atoms, or a peptide or peptidomimetic moiety containing 10 to about 30 carbon atoms.

In yet another embodiment, the present inventive method further comprises administering a composition comprising a nonsense codon suppression agent in an amount effective to inhibit translation termination at a misplaced nonsense mutation.

In another aspect, the invention provides a method of treating a NAD comprising administering to a patient suffering from a NAD a composition comprising an RNA interference agent capable of inhibiting the expression of eIF5A, DOHH and/or DHS. In different embodiments, the RNA interference agent may be selected from antisense oligonucleotides, siRNA, shRNA, and/or DNA constructs encoding same.

In yet another aspect, the invention provides a method of detecting a nonsense mutation, the method comprising obtaining a cell sample from a patient, treating said sample with an inhibitor of eIF5A, preferably culturing said cells under time and conditions sufficient to generate nonsense mRNA encoding a prematurely truncated protein, extracting said mRNA, preparing a cDNA from said mRNA, and analyzing the resulting cDNA. The inhibitor of eIF5A may be a direct inhibitor (e.g., a siRNA targeting eIF5A mRNA) or an indirect inhibitor (e.g., a siRNA targeting DOHH or DHS mRNAs). In other embodiments, the inhibitor may be selected from the compounds of Formulae I-IV with limitations specified above.

DETAILED DESCRIPTION OF THE INVENTION

Figure 1:
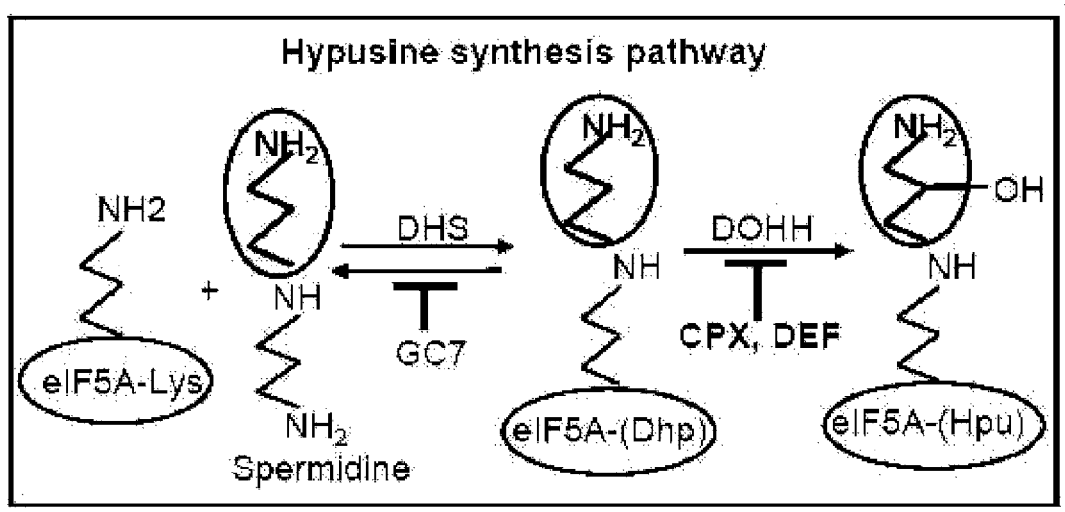
FIG. 1 illustrates the hypusine synthesis pathway of eIF5A.

As used herein, the following terms, unless otherwise indicated, shall be understood to have the following meaning:

"Biological agent" or "biological agents" include any agent known in the art such as, but not limited to, proteins or protein-based molecule, such as a mutant ligand, antibody, or the like, and nucleic acids or nucleic acid-based entities and the vectors used for their delivery.

"Compound" or "compounds" refers to conventional chemical compounds (e.g., small organic or inorganic molecules). To this end, the terms small molecule and compounds are interchangeable.

"Effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state.

"Nonsense-mediated decay" ("NMD") refers to a cellular mechanism that selectively degrades faulty messenger RNA ("mRNA") containing an out-of-place stop (nonsense) codon.

"Nonsense-associated disease" ("NAD") refers to a genetic disorder characterized by premature stop mutations that often lead to a complete loss of protein function and a severe reduction in mRNA levels due to NMD.

"NMD inhibitor" refers to a compound or any biological agent that decreases the activity of NMD in a cell and decreases the destruction of defective mRNA by any measurable amount, as compared to such a cell in the absence of such an inhibitor. NMD inhibitors may include, but are not limited, compounds that block DOHH activity.

"NAD inhibitor" refers to a compound or any biological agent that mitigates, inhibits, and/or prevents symptoms of a NAD.

A compound or agent is said to be "harmful to biological function" if it is harmful or otherwise damaging to a biological pathway. For example, as applied to the instant application, the prematurely terminated protein may be harmful to a biological function if it affects the relevant biological pathway, e.g., by competing with the normal protein or exerting a dominant-negative effect. Prematurely terminated proteins which do not exert their normal function without actively interfering with the relevant biological pathway are not harmful to biological function.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

As used herein, with respect to administering an inhibitor, the terms "mitigate" or "mitigating" refers to reducing the progression and symptoms of a NAD. It may include executing a protocol, which may include administering one or more drugs to a patient (human or otherwise), in an effort to reduce signs or symptoms of the NAD.

As used herein, with respect to administering an inhibitor, the terms "prevent," or "preventing" refers to prophylactic treatment for halting a disease or condition. It may include executing a protocol, which may include administering one or more drugs to a patient (human or otherwise), in an effort to prevent signs or symptoms of the disease. In certain embodiments, prophylactic treatment prevents worsening of a disease or condition.

"Subject" refers to any animal (e.g., a mammal), including, but not limited to humans, non-human primates, rodents, and any other animal, which is to be the recipient of a particular treatment. Typically, the terms "subject" and "patient" are used interchangeably herein in reference to a human subject.

As used herein, with respect to administering an inhibitor, the terms "treat," "treating," or "treatment" refers to therapeutic treatment for halting or reducing a disease or condition. It may include executing a protocol, which may include administering one or more drugs to a patient (human or otherwise), in an effort to alleviate signs or symptoms of the disease. In certain embodiments, therapeutic treatment prevents worsening of a disease or condition.

The present invention relates to methods of treating a NAD by preventing, mitigating, and/or inhibiting NMD. The present invention further relates to compounds and pharmaceutical compositions which are highly effective at preventing, mitigating, and/or inhibiting NMD. More specifically, the instant invention relates to preventing, mitigating, and/or inhibiting NMD by inhibiting the formation of the hypusine residue in cellular eIF5A precursor proteins.

Inhibition of NMD provides a mechanism to remediate an inherited disease by transcript stabilization, provided that the upstream nonsense codon is positioned such that the truncated protein has a beneficial biological effect. Likewise, inhibition of NMD provides a mechanism to remediate an acquired disease by transcript emergence, provided that the upstream nonsense codon is positioned such that the cryptic protein has a beneficial biological effect. Applicants have come to recognize that eIF5A is one protein involved in NMD, and that inhibition of eIF5A causes inhibition of the NMD pathway, thereby increasing the amount of NMD-susceptible mRNA, which results in the mitigation of NAD symptoms. In other cases, in which the truncated protein does not have a beneficial biological effect, inhibition of NMD leading to increased amount of the mRNA will be combined with stop codon suppression to cause production of full-length protein.

Approximately 33% of genetic and acquired diseases are NADs. The methods of the present invention relate to treating such NADs including, but not limited to, lysosomal disorders (e.g., Niemann-Pick disease), metabolism disorders (e.g., familial hypercholesterolemia and McArdle disease), familial cancer syndromes (e.g., retinoblastoma and breast cancer), neurodegenerative disorders (e.g., amyotrophic lateral sclerosis and spastic paraplegia), muscular disorders (congenital muscular dystrophy and autosomal recessive proximal spinal muscular atrophy), connective tissues disorders (Ehlers Danlos Syndrome), secretory disorders (e.g., cystic fibrosis), hematologic diseases (e.g., thalassemia), primary immunodeficiency disorders (e.g. ataxia-telangiectasia) and cardiovascular diseases (e.g., long QT syndrome and ischemia syndrome). Examples of other NADs include, but are not limited to, collagenopathies, frontotemporal dementia, Tay-Sachs disease, Parkinson disease, Smith-Lemli-Opitz syndrome, Alagille syndrome, and Carney complex. Additionally, methods of the present invention also relate to treatment of various acquired diseases and infectious disorders (e.g., retrocyclin "reawakening" to curtail HIV transmission). Moreover, NMD is likely to be responsible for at least some cases of diverse diseases including cancer. Methods of the present invention apply to any disease resulting from decreased mRNA production or stability that could be treated.

In a further embodiment, the present invention relates to the treatment of NADs characterized by prematurely terminated proteins that are not harmful to biological functions.

In one embodiment, it is therapeutically sufficient to decrease the symptoms of a NAD by inhibition of NMD, thereby increasing the amount of protein generated from otherwise NMD-susceptible mRNA. In other embodiments it is therapeutically sufficient to decrease the symptoms of a NAD by combination therapy in which NAD symptoms are decreased by both NMD inhibition and by suppressing nonsense codon recognition. Non-limiting examples of compounds capable of suppressing nonsense codon recognition are embodied by select aminoglycoside antibiotics (e.g. gentamicin) or the experimental agent PTC124 (Ataluren™) These compounds cause ribosome readthrough at the site of the nonsense stop codon in defective RNA, but are themselves either ineffective or inconsistently effective for treatment of NADs due to the efficient NMD-mediated destruction of defective RNA in at least a large subset of NAD-relevant cells. However, if NMD-mediated destruction of defective RNA is rendered inefficient (e.g. by downregulation of NMD), readthrough-enhancing drugs cause synthesis of full-length protein and mitigation of symptoms in NADs.

Maturation of eIF5A involves both acetylation and hypusination and is necessary for most, if not all, of its biological roles. With reference to FIG. 1, hypusine is formed by the posttranslational modification of a specific lysine residue in both eIF5A isoforms. This modification of eIF5A entails two consecutive steps. In the first step, deoxyhypusine synthase ("DHS") catalyzes the cleavage of the polyamine spermidine and the transfer of its 3-aminobutyl moiety to the ε-amino group of lysine-50 of the eIF5A precursor, yielding a deoxyhypusine-containing intermediate. In the second step, deoxyhypusine hydroxylase ("DOHH") hydroxylates the deoxyhypusyl-eIF5A intermediate to hypusine-containing mature eIF5A using molecular oxygen. The non-heme iron in the catalytic center of DOHH renders the enzyme susceptible to small molecule inhibitors that conform to the steric restrictions imposed by the active site pocket and interact with the metal via bidentate coordination.

In one embodiment, the present invention relates to therapeutic compositions and methods that employ compounds and compositions that inhibit the posttranslational formation of hypusine-containing mature eIF5A. With reference to FIG. 1, the inhibition of posttranslation formation of mature eIF5A is achieved by blocking either DHS or DOHH activity. For example, and not by way of limitation, Applicants have come to recognize that DHS activity is inhibited by GC7, and DOHH activity is inhibited by ciclopirox ("CPX") and deferiprone ("DEF"). Such inhibition suppresses NMD activity that contributes to NADs. The methods of the present invention involve administering, to eukaryotic cells, tissues, or individuals, compounds which block the posttranslational intracellular formation of hypusine, in an amount effective to suppress synthesis of bioactive eIF5A or its bioactive isoforms.

One embodiment of the present invention is a therapeutic composition or a pharmaceutical composition comprising a N-hydroxypyrid-2-one compound of formula (I) and derivatives thereof (including salts, solvates, and tautomeric forms):

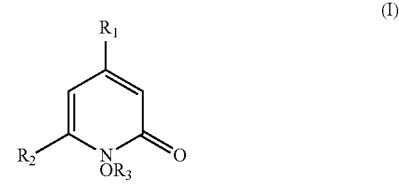

(I)

wherein
R$_1$ is (C$_1$-C$_6$)alkyl;
R$_2$ is (C$_1$-C$_{10}$) straight or branched alkyl, (C$_3$-C$_6$)cycloalkyl or phenoxy(C$_1$-C$_3$)alkyl, where the phenoxy group is substituted by substituted or unsubstituted phenoxy; and
R$_3$ is hydrogen or a pharmacologically acceptable salt.
Preferably, R$_1$ is methyl.
More preferably, R$_1$ is methyl, R$_2$ is cyclohexyl or

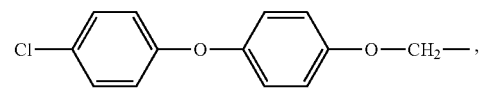 [SMILES: CCOc1ccc(Oc2ccc(Cl)cc2)cc1]

and R$_3$ is hydrogen.
In another embodiment, R$_1$ is methyl, R$_2$ is (CH$_3$)$_3$CCH$_2$(CH$_3$)CH$_2$— and R$_3$ is $^+$H$_3$NCH$_2$OH.

Examples of such compounds and salts thereof of formula (I) useful in the practice of the present invention include, but are not limited to, ciclopirox (CAS #29342-05-0), ribopirox (CAS #104153-37-9) and their analogs, such as metipirox (CAS #29342-02-7) or piroctone (CAS #506050-75-5); as well as their (1:1) ethanolamine salts, exemplified by octopirox (CAS #68890-6-4).

In one preferred embodiment, compounds of formula (I) comprise ciclopirox ("CPX") and its analogues:

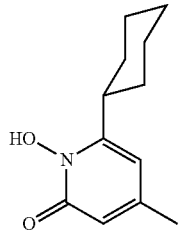

CPX is a topical antifungal (e.g., Batrafen™).

Another embodiment of the present invention is a therapeutic composition or a pharmaceutical composition comprising a thiazoline-4-carboxylic acid compound of formula (II) and derivatives thereof (including salts, solvates, and tautomeric forms):

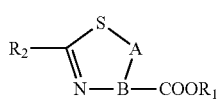

(II)

wherein $R_1$ is hydrogen or a pharmacologically acceptable salt;

$R_2$ is ortho hydroxyl-substituted phenyl or pyridyl, where the phenyl or pyridyl group is otherwise unsubstituted or substituted with 1 to 3 additional substituents selected from the group consisting of $(C_1-C_6)$alkyl, phenyl, $(C_1-C_6)$alkoxy, halogen, or hydroxyl;

A-B is —$CH_2$—$CR_3$— or —CH=CH—; and $R_3$ is hydrogen or $(C_1-C_6)$alkyl.

In on embodiment of the invention, $R_1$ is hydrogen, $R_2$ is phenyl, A-B is —CH=$CR_3$—, and $R_3$ is hydrogen. More preferably, $R_2$ is 2-hydroxyl-4-methylphenyl or 2,4-dihydroxyphenyl.

Another embodiment of the present invention is a therapeutic composition or a pharmaceutical composition comprising a compound of formula (III) or (IV):

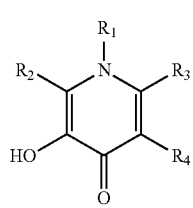

(III)

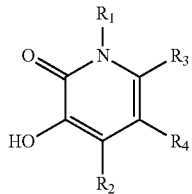

(IV)

wherein $R_1$, $R_2$, $R_3$, and $R_4$ each individually represent a hydrogen, an alkyl, alkenyl or alkoxy group containing 1 to about 8 carbon atoms, an aryl, arylalkyl, cycloalkyl group containing about 5 to 12 carbon atoms, or a carboalkoxy or carbamyl group containing up to 8 carbon atoms, or a peptide or peptidomimetic moiety containing 10 to about 30 carbon atoms.

In a preferred embodiment, compounds of formula (III) and (IV) comprise deferiprone ("DEF") and its analogues:

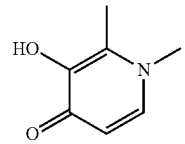

DEF is a medicinal chelator (e.g., Ferriprox™) taken orally for systemic iron overload.

These compounds may be made by the methods disclosed in U.S. Pat. No. 2,540,218 and U.S. Pat. No. 4,797,409, the contents of which are incorporated herein by reference in their entirety.

The hydroxypyridones of the present invention may be used in the free form or as their physiologically tolerated salts with inorganic or organic bases, such as, but not limited to, NaOH, KOH, Ca(OH)$_2$, NH$_3$, and H$_2$NCH$_2$CH$_2$OH.

For purposes of the present inventive methods, the amount or dose of the compound administered should be sufficient to affect a therapeutic response in the animal over a reasonable time frame. Particularly, the dose of any composition including one or more of the compounds of any of formula (I)-(IV) should be sufficient to inhibit formation of hypusine in the precursor protein of eIF5A within about 24 hours. The dose will be determined by the efficacy of the particular compound and the condition of the patient, tissue, or cell sample as well as the mass of the sample or patient to be treated. Many assays for determining an administered dose are known in the art.

For purposes of the present invention, an assay which comprises comparing the extent to which disruption of the NMD pathway increases gene expression can be used to determine a starting dose to be administered. Depletion of eIF5A by RNA silencing inhibits NMD, resulting in an increase in gene expression of NMD sensitive constructs. Such assays measure expression from constructs that carry 3' signals known to confer NMD sensitivity or insensitivity. Those constructs that are sensitive to NMD generate approximately 5-fold less mRNA. Expression from the NMD-sensitive constructs is boosted by administration of compounds that inhibit hypusination of eIF5A. In a preferred embodiment, methods of the present invention are directed to inhibition of eIF5A hypusination by compounds of formula (I)-(IV), preferably ciclopirox and deferiprone. Both ciclopirox and deferiprone are iron chelators.

In other embodiments, the method for treating a NAD comprises administering to a patient suffering from a NAD a composition comprising an RNA interference therapy agent capable of inhibiting at least one of eIF5A, DOHH or DHS.

The RNA interfering agent may be an antisense nucleotide, siRNA, shRNA, or a DNA construct (e.g., a plasmid or a vector) encoding same.

siRNAs are double stranded RNA agents that have complementary to (i.e., able to base-pair with) a portion of the target mRNA. shRNA molecules are basically siRNA molecules wherein the two strands are connected by a loop thereby resulting in a formation of a hairpin-like structure. Generally, complementarity to the target is 100%, but can be less if desired, such as 91%, 92%, 93%, 94%, 95%, 96%, 97%, 98%, or 99%. For example, 19 bases out of 21 bases may be base-paired. In some instances, where selection between various allelic variants is desired, 100% complementary to the target gene is required in order to effectively discern the target sequence from the other allelic sequence. When selecting between allelic targets, choice of length is also an important factor because it is the other factor involved in the percent complementary and the ability to differentiate between allelic differences The small interfering RNA sequence needs to be of sufficient length to bring the small interfering RNA and target RNA together through complementary base-pairing interactions. The small interfering RNA of the invention may be of varying lengths. The length of the small interfering RNA is preferably greater than or equal to ten nucleotides and of sufficient length to stably interact with the target RNA; specifically 15-30 nucleotides; more specifically any integer between 15 and 30 nucleotides, such as 15, 16, 17, 18, 19, 20, 21, 22, 23, 24, 25, 26, 27, 28, 29, and 30.

A person of ordinary skill in the art would be able to select an active RNA interfering agent based on the facts that sequences for eIF5A, DOHH and DHS are well known in the art and available from public databases and that criteria for selection of active RNA interference agents are known in the art. For example, US Publication 20070031844 by Khvorova et al. or US Publication 20060275762 by Saigo et al. disclose some criteria for selection of active siRNAs.

In other embodiments, siRNAs or antisense oligonucleotides may be used to inhibit the expression of enzymes DOHH and/or DHS that modulate the activity of eIF5A. The criteria for selection of active antisense oligonucleotides are also known in the art. For example, it is known that regions having high G-C content are usually not good candidates for antisense oligonucleotides.

The nucleic acid sequence encoding the active antisense, siRNA, or shRNA may be incorporated within a vector, preferably, a viral vector. Suitable vectors include, without limitations, adeno-associated viral vector, retroviral vectors, or adenoviral vectors. The methods of subcloning the sequences encoding the active RNA interference agents are also well known in the art.

Furthermore, all of the present inventive methods can comprise the administration of the compound, in the presence or absence of an agent that enhances its efficacy, or the methods can further comprise the administration of other suitable components, such as compounds that suppress nonsense codon recognition. Such suppression reduces the efficiency of translation termination at the misplaced nonsense mutations by administering certain pharmacological compounds or suppressor tRNAs. Examples of suppressor tRNAs and other pharmacological compounds that suppress nonsense mutations should be readily apparent to one skilled in the art.

One of ordinary skill in the art will readily appreciate that each compound of the present inventive methods can be modified in any number of ways, such that the therapeutic efficacy of the compound is increased through the modification. For instance, the compound could be conjugated either directly or indirectly through a linker to a targeting moiety. The practice of conjugating compounds to targeting moieties is known in the art. See, e.g., Wada et al., J. Drug Targeting, 3:111 (1995); U.S. Pat. No. 5,087,616; and U.S. Pat. No. 5,849,587, the contents of which are incorporated herein by reference in their entirety. The term "targeting moiety" as used herein, refers to any molecule or agent that specifically recognizes and binds to a cell-surface receptor, such that the targeting moiety directs the delivery of the compound to a population of cells on which surface the receptor is expressed. Targeting moieties include, but are not limited to, antibodies, or fragments thereof, peptides, hormones, growth factors, cytokines, and any other naturally or non-naturally existing ligands, which bind to cell surface receptors. The term "linker" as used herein, refers to any agent or molecule that bridges the compound to the targeting moiety.

One of ordinary skill in the art recognizes that sites on the compounds, which are not necessary for the function of the compound, are ideal sites for attaching a linker and/or a targeting moiety, provided that the linker and/or targeting moiety, once attached to the compound does not interfere with the function of the compound, i.e., the ability to inhibit formation of the hypusine residue and form eIF5A.

One skilled in the art will appreciate that suitable methods of administering a compound of the present invention are known, and, although more than one route can be used to administer a particular composition, a particular route can provide a more immediate and more effective response than another route.

In the practice of the present invention, compositions that include compounds of formula (I)-(IV) can be administered topically or systemically (intravenously or subcutaneously). More particularly, such administration can be orally; parenterally, i.e., by subcutaneous, intravascular, or intramuscular injection; intraperitoneally; intrathecally; or by topical application, e.g., to skin or eyes, or by application to the mucous membranes of the nose, throat, bronchial tree, genital tract, or rectum, and so forth. They may be administered alone or with suitable pharmaceutical carriers, and can be in solid or liquid form such as tablets, capsules, powders, solutions, suspensions, or emulsions.

The size of the dosage of the compound of the present invention will also be determined by the existence, nature and extent of any adverse side effects that might accompany the administration of a particular compound. Ultimately, the attending physician will decide the dosage of the compound of the present invention with which to treat each individual patient, taking into consideration a variety of factors, such as age, body weight, general health, diet, sex, inhibitor to be administered, route of administration, and the severity of the condition being treated.

Formulations suitable for oral administration of compositions which include compounds of the present invention can consist of (a) liquid solutions, such as an effective amount of the compounds dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch potato starch, microcrystalline cellulose, acacia, gelatin, colloidal silicon dioxide, croscarmellose, sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Formulations of the compounds of formula (I)-(IV) in compositions suitable for parenteral administration (subcutaneous, intravascular, or intramuscular injection) include aqueous and non-aqueous solutions, isotonic sterile injection solutions, which can contain antioxidants, buffers, bacteriostats, and solutes that render the formulation isotonic with the blood of the intended recipient, and aqueous and non-aqueous solutions, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described. In general, water, saline, aqueous dextrose and related sugar solution, and glycols such as propylene glycol or polyethylene glycol, are preferred liquid carriers, particularly for injectable solutions.

The pharmaceutical products of the present invention are prepared by dissolving, mixing, granulating, or tablet-coating processes known to those skilled in the art. For oral administration, the active compounds or their physiologically tolerated derivatives such as salts, esters, or amides, are mixed with the additives customary for this purpose, such as vehicles, stabilizers, or inert diluents, and are converted by customary methods into a suitable form for administration, such as tablets, coated tablets, hard or soft gelatin capsules, aqueous, alcoholic, or oily suspensions, or aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant like stearic acid or magnesium stearate. Examples of suitable oily vehicles or solvents are vegetable or animal oils, such as sunflower oil or fish-liver oil. Preparations can be effected both as dry and as wet granules.

For use as aerosols, the active compounds or their physiologically tolerated derivatives such as salts, esters, or amides, may be dissolved or suspended in a physiologically acceptable liquid and packaged in a pressurized aerosol container together with suitable propellants, for example, hydrocarbon propellants like propane, butane, or isobutane with conventional adjuvants. The agents which block intracellular hypusine formation, in accordance with the present invention, may also be administered from a non-pressurized container such as a nebulizer or atomizer.

For topical administration to external or internal body surfaces, e.g., in the form of creams, gels, or drops, and so forth, the active compounds or their physiologically tolerated derivatives such as, salts, esters, or amides, are prepared and applied as solutions, suspensions, or emulsions in a physiologically acceptable diluent with or without a pharmaceutical carrier.

Diagnostics of nonsense mutations is complicated due to NMD which removes the defective mRNA. However, once NMD is inhibited, e.g., by inhibition of eIF5A, the relative number of defective mRNA templates is increased. As a result, signal-to-noise ratio is also increased thus allowing for a more reliable detection of such nonsense-mutated mRNA and thus for actionable diagnostic information.

Accordingly, in one embodiment, the method comprises obtaining a cell sample from a patient, treating said sample with an inhibitor of eIF5A, preferably culturing said cells under time and conditions sufficient to express nonsense mRNA encoding a prematurely truncated protein, extracting said mRNA, preparing a cDNA from said mRNA, and analyzing the resulting cDNA, e.g., by restriction analysis or by sequencing.

According to this aspect, the cell sample should comprise cells where the mRNA containing premature stop codon is expressed, and therefore, the nature of the cell sample would ultimately depend on the nature of the mRNA which is to be tested. The means for inhibiting eIF5A are also known in the art and/or discussed in the instant specification. For example, in certain embodiments, eIF5A may be inhibited using the compounds according to the Formulae I-IV, with the limitations for the side chain substitutions as described above.

In other embodiments, RNAi agents may be used, such as antisense nucleotides and/or siRNA (or shRNA). As noted above, the sequences for the suitable targets (eIF5A, DOHH and DHS) are well known in the art, and the algorithms for selecting suitable RNA interference agents are also described in the prior art. Similarly, the methods of culturing cells, extracting mRNA, and obtaining cDNA from mRNA are well known and do not need to be described in details herein.

The following non-limiting examples set forth below illustrate certain aspects of the invention. These examples are illustrative only, and are not intended to limit the remainder of the disclosure in any way.

EXAMPLES

Example 1

Prevention of Maturation of eIF5A by Inhibition of DOHH

To examine the effect of compounds on the synthesis of modified eIF5A, 293T cells transfected with a FLAG-tagged eIF5A expression vector were simultaneously treated with ciclopirox ("CPX") or deferiprone ("DEF").

FLAG-eIF5A was monitored using NIH-353 and anti-FLAG antibodies (FIGS. 2A and 2B). FIG. 2A illustrates inhibition of eIF5A modification in 293T cells. Cells transfected with FLAG-tagged eIF5A were untreated or treated with increasing concentrations of CPX as indicated, or with agent P2. FIG. 2B illustrates cells transfected with FLAG-tagged eIF5A that were untreated or treated with increasing concentrations of DEF as indicated, or with DFOX. At 24 hours post-transfection, whole cell extract ("WCE") was analyzed by immunoblotting with the NIH-353 anti-eIF5A antibody (upper panel) and anti-actin antibody (lower panel). The NIH-335 antibody reacts preferentially with post-translationally modified eIF5A. CPX reduced the appearance of mature eIF5A over the 3-30 μM concentration range, while DEF was effective at 200-400 μM. The compounds did not alter the expression of actin. Comparable results have been obtained in other cell types by spermidine labeling of eIF5A. In addition to the CPX homolog Agent P2, deferoxamine ("DFOX"; Desferal™) was used as a control compound. DFOX, a metal-binding hydroxamate like CPX and Agent P2 (FIG. 3), is a globally used medicinal iron chelator. Referring to FIGS. 2A and 2B, in contrast to CPX and DEF, P2 and DFOX had little or no effect on the appearance of mature FLAG-eIF5A (FIGS. 2A and 2B), indicating that the ability to chelate iron is insufficient to inhibit DOHH and the maturation of eIF5A.

FIG. 2C illustrates cells transfected with FLAG-tagged eIF5A that were treated with CPX (30 µM), P2 (30 µM), DEF (250 µM), DFOX (10 µM), or no compound (−). At 24 hours post-transfection, WCE was analyzed by immunoblotting with the NIH-353 anti-eIF5A antibody (upper panel) and anti-FLAG antibody (lower panel). The control culture was transfected with empty vector and no compound was added. None of these compounds reduced the overall expression of the FLAG-eIF5A protein detectably (FIG. 2C), ruling out general inhibitory effects on gene expression. Based on these results, 30 µM CPX and 250 µM DEF were used for subsequent experiments.

These results indicate that eIF5A forms tight complexes with its modifying enzymes. Unmodified eIF5A (lysine-50) immunoprecipitates with DHS, and deoxyhypusyl-eIF5A interacts with DOHH in vitro. The deoxyhypusyl-eIF5A:DOHH complex formed in vivo can be detected by immunoprecipitation from cell extracts. Taking advantage of this finding, the effects of the compounds on the enzyme-substrate interaction was tested, the results of which are illustrated in FIG. 2D. FLAG-eIF5A was expressed in 293T cells. 293T cells transfected with FLAG-eIF5A were untreated (−) or treated with GC7 (10 µM) or CPX (30 µM), P2 (30 µM), DEF (250 µM), or DFOX (10 µM). WCE prepared at 24 hours post-transfection was immunoprecipitated with anti-FLAG antibody. Complexes that immunoprecipitated with anti-FLAG antibody were immunoblotted and probed with antibodies against DOHH. Endogenous DOHH co-immunoprecipitated with FLAG-eIF5A, and this association was largely prevented by treatment with CPX or DEF (FIG. 2D, top panel). Consistent with their inability to inhibit eIF5A maturation, neither P2 or DFOX prevented the formation of the eIF5A:DOHH complex. As a further control, the DHS inhibitor GC7 was included in this assay. No DOHH was associated with FLAG-eIF5A in the presence of GC7 because it prevents the synthesis of deoxyhypusyl-eIF5A. As expected, none of the compounds affected the immunoprecipitation of FLAG-eIF5A (FIG. 2D, middle panel; note that the band marked with an asterisk (*) is background due to IgG light chain) or the expression of endogenous eIF5A (FIG. 2D, bottom panel).

FIG. 2E illustrates 293T cells transfected with FLAG-DHS, FLAG-DOHH or empty vector (control) were treated with GC7, CPX, or DEF, or no drug (−) at the same concentration as in FIG. 2D. Immunoprecipitates obtained with anti-FLAG antibody were immunoblotted and probed with anti-eIF5A antibody (BD). WCE equivalent to 5% of the input was immunoblotted as a further control. Reciprocally, the interaction between endogenous eIF5A and tagged DOHH was inhibited by CPX and DEF (FIG. 2E, right). Similarly, the interaction of endogenous eIF5A with tagged DHS was inhibited by GC7 (FIG. 2E, left), but was resistant to CPX and DEF (not shown).

These results demonstrate that CPX and DEF, but not P2 or DFOX, target DOHH and inhibit its interaction with its substrate, deoxyhypusyl-eIF5A. Despite divergent chemical structures, CPX and DEF both act as potent inhibitors of eIF5A maturation in cells and in vitro. DEF is in clinical use as an orally active medicinal chelator for treatment of transfusion-related iron overload, and CPX is employed as a topical antifungal. After oral medication, the concentration of DEF in serum can reach and exceed 250 µM. The topical preparations of CPX, which contain up to 57.5 mM of the agent, achieve levels in excess of 30 µM in skin. These results were obtained at 250 µM DEF and 30 µM CPX, concentrations well within the range of the compounds' clinically relevant levels. At these concentrations, CPX and DEF can reduce bioavailable intracellular iron levels as determined with an iron-sensitive reporter system. Agent P2, a bidentate chelation homolog of CPX lacking its hydrophobic cyclohexyl group, displayed little or no activity in cell-based assays. Thus, the inhibitory action of CPX and DEF on eIF5A is not merely a consequence of their ability to coordinate and deplete bioavailable iron by bidentate chelation.

Figure 2:
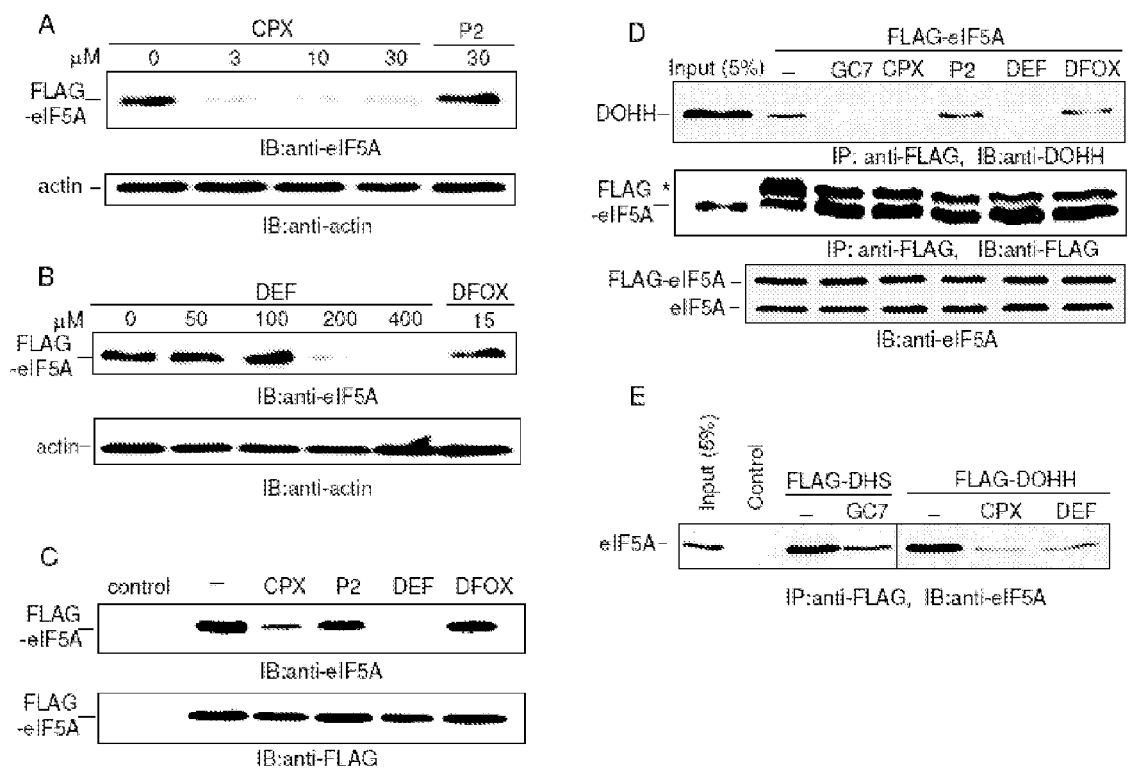
FIG. 2 illustrates the effects of ciclopirox and deferiprone on eIF5A and DOHH.
Figure 3:
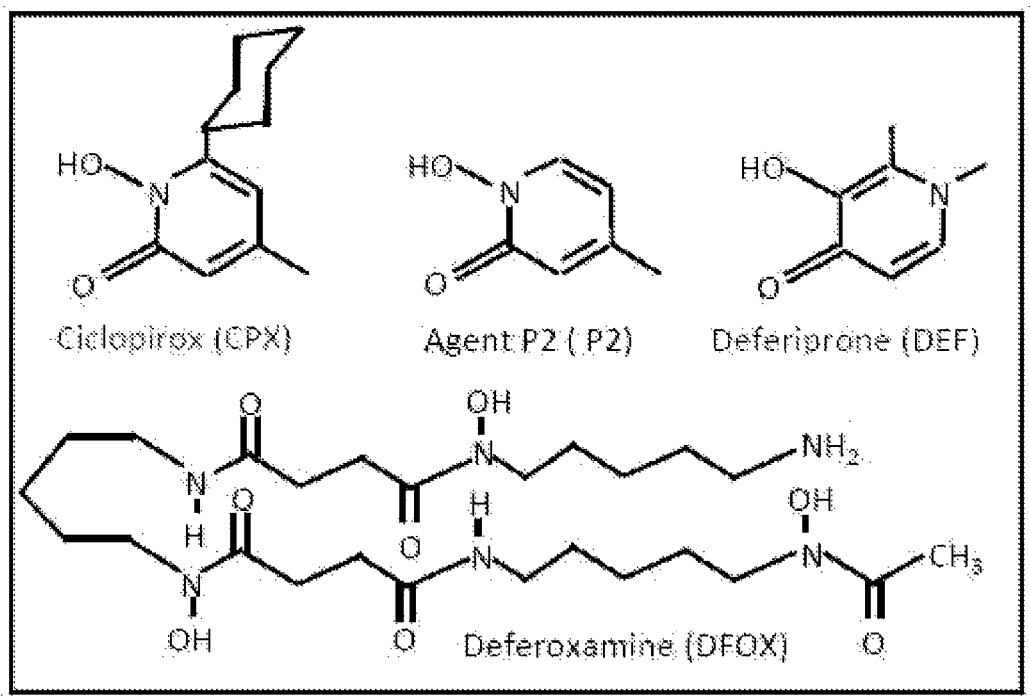
FIG. 3 illustrates various compounds and control compounds that can be used to demonstrate inhibition of eIF5A.

CPX and DEF destabilized the interaction between DOHH and deoxyhypusyl-eIF5A, resulting in a marked decrease in the appearance of newly synthesized mature eIF5A (FIG. 2). The drugs did not prevent eIF5A from forming a complex with DHS, which is consistent with the accumulation of deoxyhypusyl-eIF5A in the presence of either drug at concentrations that completely blocked DOHH activity. Neither DFOX nor P2 had any effect on the binding of eIF5A to DOHH, in accordance with their failure to inhibit the formation of hypusinyl-eIF5A. On the other hand, the DHS inhibitor GC7 blocked formation of lysyl-eIF5A:DHS complexes, causing a marked decrease in the levels of deoxyhypusyl-eIF5A and its complexes with DOHH. These findings, supported by molecular modeling, indicate that CPX and DEF enter the deoxyhypusine-binding pocket of DOHH, become oriented towards its catalytic iron atom and chelate it. The compound-iron chelate is then released from the apoenzyme, which irreversibly collapses into a catalytically inactive molecule incapable of binding substrate. Supporting this mechanism, DEF is known to cause release of peptide-bound iron from several non-heme metalloproteins, among them mono- and diferric transferrin, cyclooxygenase, and lipoxygenase.

Example 2

NMD Decreases Gene Expression at both the RNA and Protein Levels

Figure 4:
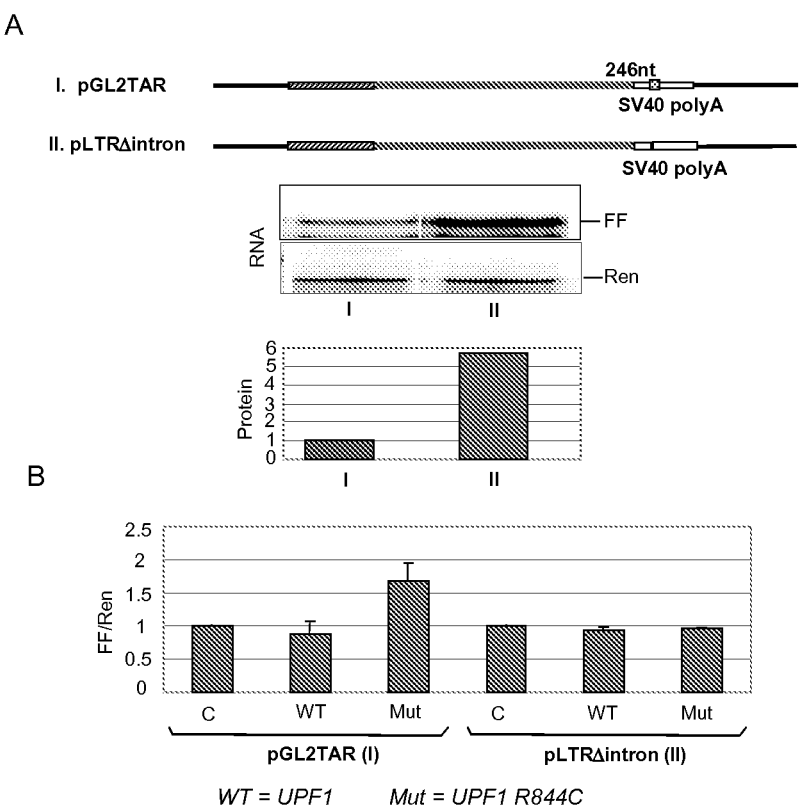
FIG. 4 demonstrates that NMD decreases gene expression at both the RNA and protein levels.

Human 293 cells were co-transfected with a test plasmid (construct I) that is sensitive to NMD and a matched control plasmid (construct II). The constructs contain firefly luciferase (FF) reporter genes and are based on studies in the HIV-1 system (Hoque M, Hanauske-Abel H M, Palumbo P, Saxena D, D'Alliessi Gandolfi D, Park M H, Pe'ery T, Mathews M B. Retrovirology. 2009 Oct. 13; 6:90). A plasmid expressing Renilla luciferase (Ren) directed by the CMV promoter was included as a reference and internal control. RNA was analyzed by RNase protection assay and an autoradiograph of the results is shown. More FF RNA was generated from the NMD-insensitive construct (construct I) than from the NMD-sensitive construct (construct II). Similar observations were made at the protein level. Luciferase proteins were analyzed by dual luciferase assay kit (Promega) and the data are illustrated as the firefly: Renilla ratio. An inactive (dominant negative) mutant of the Upf1 protein, known to be required for NMD, inhibited NMD in this construct system (FIG. 4B). The results are shown as firefly: Renilla luciferase ratio (FF/Ren). Taken together, these data verify that the assay is measuring NMD.

Figure 5:
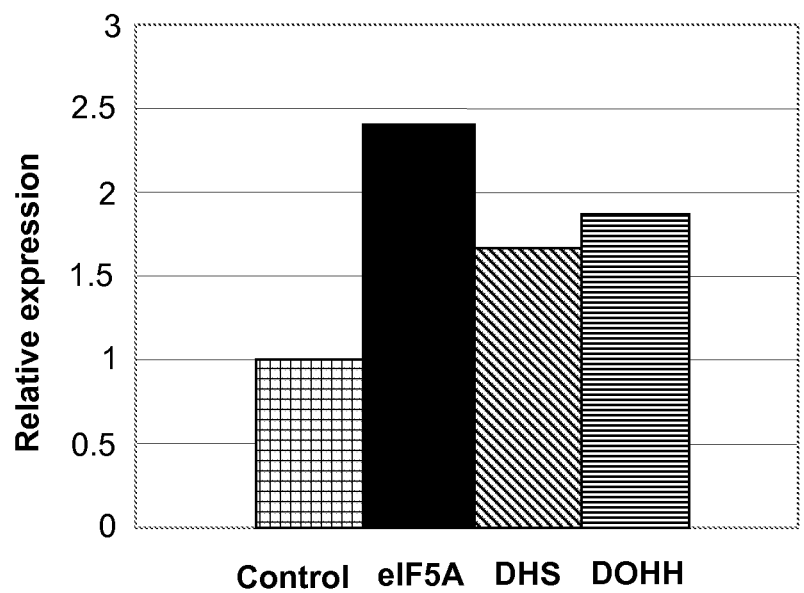
FIG. 5 demonstrates that depletion of eIF5A, DHS or DOHH inhibited NMD and therefore increased gene expression from the NMD-sensitive construct in U2OS human osteosarcoma cells.

It was important to demonstrate that hypusine-modified eIF5A is involved in NMD. The experiment of FIG. 5 used RNA silencing with small interfering RNAs (siRNAs) to deplete eIF5A itself, or either of the modifying enzymes required for hypusine formation. Depletion of U2OS human osteosarcoma cells for eIF5A, DHS or DOHH inhibited NMD and therefore increased gene expression from the NMD-sensitive construct. Data are shown as ratio of luciferase activities. Similar results were obtained with a plasmid containing naturally-occurring beta-globin mutations. These results show that hypusine-containing eIF5A is involved in NMD.

Figure 6:
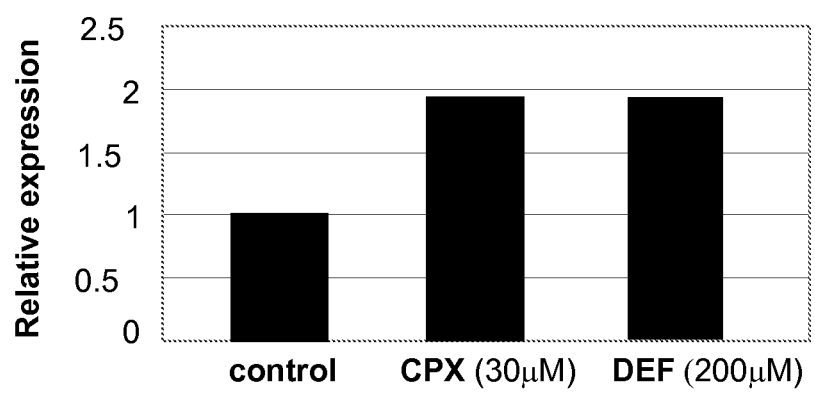
FIG. 6 demonstrates that NMD is inhibited by the drugs CPX and DEF, which prevent eIF5A modification

FIG. 6 shows that NMD is inhibited by the drugs CPX and DEF, which prevent eIF5A modification. This inhibition is seen at drug concentrations that interfere with DOHH function, namely 30 μM CPX and 200 μM DEF. This experiment was carried out in a well-authenticated assay system using vectors containing NMD signals associated with beta thalassemia (Woeller C F, Gaspari M, Isken O, Maquat L.: EMBO Rep. 2008 May; 9(5):446-51.). Results are presented as a ratio of Renilla luciferase from the NMD-sensitive reporter to a matched NMD-insensitive control.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

We claim:

1. A method for treating a NAD comprising administering to a patient suffering from a NAD a composition comprising an eIF5A inhibitor compound in an amount effective to prevent intracellular hypusination of eIF5A, whereby gene expression of NMD-susceptible mRNA is increased.

2. The method of claim 1, wherein said eIF5A inhibitor compound is a compound of formula (I):

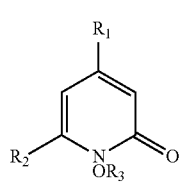

(I)

wherein
R$_1$ is (C$_1$-C$_6$) alkyl;
R$_2$ is (C$_1$-C$_{10}$) straight or branched alkyl, (C$_3$-C$_6$)cycloalkyl or phenoxy(C$_1$-C$_3$)alkyl, where the phenoxy group is substituted by substituted or unsubstituted phenoxy; and
R$_3$ is hydrogen or a pharmacologically acceptable salt.

3. The method of claim 2, wherein R$_1$ is methyl, R$_2$ is cyclohexyl, and R$_3$ is hydrogen.

4. The method of claim 2, wherein R$_1$ is methyl, R$_2$ is (CH$_3$)$_3$CCH$_2$(CH$_3$)CH$_2$—, and R$_3$ is $^+$H$_3$NCH$_2$OH.

5. The method of claim 1, wherein said eIF5A inhibitor compound is a compound of formula (II):

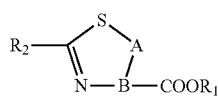

(II)

wherein
R$_1$ is hydrogen or a pharmacologically acceptable salt;
R$_2$ is ortho hydroxyl-substituted phenyl or pyridyl, where the phenyl or pyridyl group is otherwise unsubstituted or substituted with 1 to 3 additional substituents selected from the group consisting of (C$_1$-C$_6$) alkyl, phenyl, (C$_1$-C$_6$)alkoxy, halogen, or hydroxyl;
A-B is —CH$_2$—CR$_3$— or —CH=CH—; and
R$_3$ is hydrogen or (C$_1$-C$_6$)alkyl.

6. The method of claim 5, wherein R$_1$ is hydrogen, R$_2$ is phenyl, A-B is —CH=CR$_3$—, and R$_3$ is hydrogen.

7. The method of claim 1, wherein said eIF5A inhibitor compound is a compound of formula (III) or (IV):

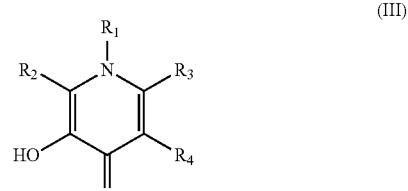

(III)

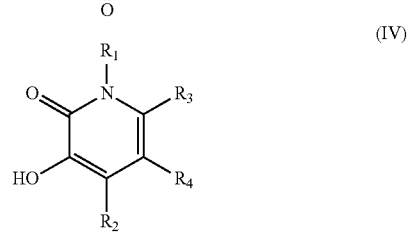

(IV)

wherein R$_1$, R$_2$, R$_3$, and R$_4$ each individually represent a hydrogen, an alkyl, alkenyl, or alkoxy group containing 1 to 8 carbon atoms, an aryl, arylaklyl, or cycloalkyl group containing 5 to 12 carbon atoms, or a peptide or peptidomimetic moiety containing 10 to 30 carbon atoms.

8. The method of claim 7, wherein said compound of formula (III) is deferiprone.

9. The method of claim 1, wherein said NAD is selected from the group consisting of lysosomal disorders, metabolism disorders, familial cancer syndromes, neurodegenerative disorders, connective tissues disorders, hematologic diseases, and cardiovascular diseases.

10. The method of claim 9, wherein said NAD is characterized by prematurely terminated proteins that are not harmful to biological functions.

11. The method of claim 1, wherein said NAD is selected from the group consisting of collagenopathies, frontotemporal dementia, Tay-Sachs disease, Parkinson disease, Smith-Lemli-Opitz syndrome, Alagille syndrome, and Carney complex.

12. The method of claim 1 further comprising administering a composition comprising a nonsense codon suppression agent in an amount effective to inhibit translation termination at a misplaced nonsense mutation.

13. The method of claim 12, wherein said nonsense codon suppression agent comprises a suppressor tRNA.

14. A method of treating a NAD comprising administering to a patient suffering from a NAD a composition comprising an eIF5A inhibitor compound, whereby gene expression of NMD-susceptible mRNA is increased, and wherein the eIF5A inhibitor compound is selected from an RNA interference agent targeting eIF5A mRNA, deoxyhypusine hydroxylase (DOHH) mRNA or deoxyhypusine synthase (DHS) mRNA.

15. The method of claim 14, wherein said RNA interference agent is selected from an antisense oligonucleotide, siRNA, shRNA, or a vector comprising a DNA sequence encoding said antisense oligonucleotide, siRNA, or shRNA.

16. The method of claim 1, wherein said NAD is selected from the group consisting of Niemann-Pick disease, familial hypercholesterolemia, McArdle disease, retinoblastoma, breast cancer, amyotrophic lateral sclerosis, spastic paraplegia, congenital muscular dystrophy, autosomal recessive proximal spinal muscular atrophy, Ehlers Danlos Syndrome, cystic fibrosis, thalassemia, ataxia-telangiectasia, long QT syndrome, ischemia syndrome and Duchene's muscular dystrophy.

17. The method of claim 1, wherein said NAD is thalassemia.

* * * * *